United States Patent

Murayama

Patent Number: 5,770,604
Date of Patent: Jun. 23, 1998

[54] ACONITINE COMPOUND AND AN ANTIPYRETIC/ANALGESIC/ANTI-INFLAMMATORY AGENT

[75] Inventor: Mitsuo Murayama, Tochigi-ken, Japan

[73] Assignee: Sanwa Shoyaku Kabushiki Kaisha, Utsunomiya, Japan

[21] Appl. No.: 530,189

[22] PCT Filed: Feb. 9, 1995

[86] PCT No.: PCT/JP95/00180

§ 371 Date: Oct. 6, 1995

§ 102(e) Date: Oct. 6, 1995

[87] PCT Pub. No.: WO95/21827

PCT Pub. Date: Aug. 17, 1995

[30] Foreign Application Priority Data

Feb. 9, 1994 [JP] Japan ................................ 6-047646

[51] Int. Cl.⁶ .................... A61K 31/435; C07D 221/22
[52] U.S. Cl. .................................... 514/279; 546/39
[58] Field of Search ........................ 546/39; 514/279

[56] References Cited

FOREIGN PATENT DOCUMENTS

| | | |
|---|---|---|
| 0 547224 A | 9/1991 | European Pat. Off. . |
| 63-211268 | 9/1988 | Japan . |
| 63-211269 | 9/1988 | Japan . |
| 64-34965 | 2/1989 | Japan . |
| 1-143859 | 6/1989 | Japan . |
| 3-223255 | 10/1991 | Japan . |
| 5-17448 | 1/1993 | Japan . |
| 6-16553 | 1/1994 | Japan . |

OTHER PUBLICATIONS

Zhang et al. Sites on Analgesic Action of 3,15–diacteylbenzoylacynine. Acta Pharmacologica Sinica, 15(2) pp. 176–180. English translation also attached, Mar. 1994.

Sato et al., "Pharmacological Actions of Aconitine Alkaloids", *Tohoku J. Exp. Med.*, vol. 128:175–187, (1979).

Primary Examiner—Robert T. Bond
Attorney, Agent, or Firm—Foley & Lardner

[57] ABSTRACT

This invention provides novel aconitine compounds of the formula (I) or salt thereof

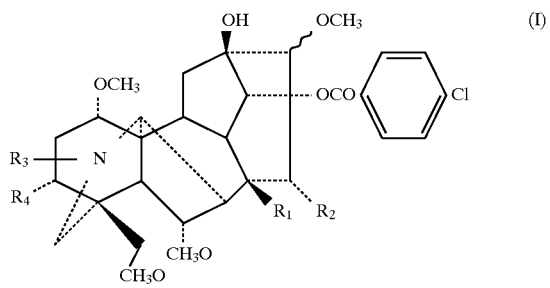

wherein, $R_1$ is a hydrogen atom or hydroxyl group; $R_2$ is an acetyloxy group; $R_3$ is an alkyl having 1–4 carbon atoms; and $R_4$ is a hydrogen atom, a hydroxyl group, or an acetyloxy group; and antipyretic/analgesic/anti-inflammatory agents containing the compound as an active ingredient which are highly safe and exhibit a powerful analgsic effect and antipyretic/anti-inflammatory activities. The compound is usable alone in painful, pyretic and inflammatory illnesses but its concomitant use with morphine reinforces the analgesic effect of morphine and allows alleviation of morphine side effects through reduction in morphine dosage.

20 Claims, No Drawings

ACONITINE COMPOUND AND AN ANTIPYRETIC/ANALGESIC/ANTI-INFLAMMATORY AGENT

This application is a 371 of PCT/JP. 95/00180, filed Feb. 9, 1995, which in turn claims priority of JAPAN 6-47648, filed Feb. 9, 1994.

TECHNICAL FIELD

The present invention relates to a novel compound possessing an aconitine chemical structure and also relates to an antipyretic/analgesic/anti-inflammatory agent containing said compound as an active ingredient. In further detail, the present invention relates to a compound possessing an aconitine chemical structure illustrated by general formula (I), or a salt thereof

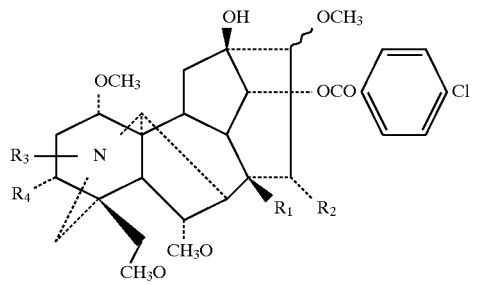

wherein,
$R_1$ is a hydrogen atom or hydroxyl group;
$R_2$ is an acetyloxy group;
$R_3$ is an alkyl having 1–4 carbon atoms; and
$R_4$ is a hydrogen atom, a hydroxyl group, or an acetyloxy group.

In addition, the present invention relates to an antipyretic/analgesic/anti-inflammatory agent characterized in that it contains as an active ingredient a novel compound possessing an aconitine chemical structure illustrated by general formula (I), or a salt thereof

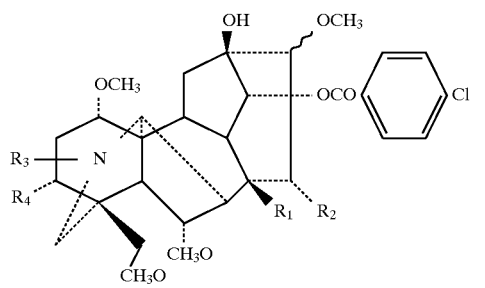

wherein,
$R_1$ is a hydrogen atom or hydroxyl group;
$R_2$ is an acetyloxy group;
$R_3$ is an alkyl having 1–4 carbon atoms; and
$R_4$ is a hydrogen atom, a hydroxyl group, or an acetyloxy group.

BACKGROUND ART

Aconitine alkaloids contained in the tuberous root of plants of the genus Aconitium have previously been reported to have potent analgesic and anti-inflammatory activity (e.g., Tohoku J. Exp. Med., 128:175–187 [1979]). However, aconitine alkaloids are highly toxic and are therefore deemed to have a narrow margin of safety.

DISCLOSURE OF INVENTION

As a result of extensive studies in attempts to obtain novel aconitine alkaloid derivatives which are low in toxicity and also retain the analgesic and anti-inflammatory activity of aconitine alkaloids, the present inventor has heretofore succeeded in offering a novel aconitine compound and an analgesic/anti-inflammatory agent (See JP, A, S63-211268, JP, A, S63-211269, JP, A, S64-34965, JP, A, H1-143859 and JP, A, H3-223255). Thereafter, the present inventor succeeded in offering an analgesic/anti-inflammatory agent containing as an active ingredient a novel analgesic/anti-inflammatory agent of 14-O-p-chlorobenzoylaconine, or a salt thereof, which exhibits activity superior to that of compounds having a p-chlorobenzoyloxy group bonded to the position 14 carbon atom of the aconitine chemical structure (See JP, A, H5-17448). As a result of further studies, the present inventor has now discovered that among compounds having a p-chlorobenzoyloxy group bonded to the position 14 carbon atom of the aconitine chemical structure, compounds having an acetyloxy group bonded to the position 15 carbon atom are particularly excellent in their pharmacological effect and are also highly safe.

Tail pressure methods and hot plate methods used for the evaluation of the analgesic activity are experimental methods applied for evaluating the activity of morphine or other such compounds having a powerful analgesic effect. The non-steroidal antipyretic/analgesics aspirin and indomethacin have a weak analgesic activity compared to morphine and are deemed to show no remarkable activity in tail pressure methods and hot plate methods. Additionally, in hot plate methods, the action of a mouse licking its paws in response to the heat stimulus provided is taken to indicate involvement of the higher central nervous system. Thus, in evaluating the analgesic effect of a compound, this method is considered a better reflect pain relief in humans than other experimental methods. In tail pressure methods and hot plate methods employing subcutaneous administration, the compound pertaining to the present invention was found to have an even stronger analgesic effect than 14-O-p-chlorobenzoylaconine and to have an antipyretic effect on rats with yeast-induced fever. Furthermore, in concomitant drug use involving intravenous administration of morphine and subcutaneous administration of the compound pertaining to the present invention, the compound pertaining to the present invention was found to strongly reinforce the analgesic effect of morphine.

Consequently, the compound pertaining to the present invention makes a great contribution to intensely painful illnesses and pyretic and inflammatory illnesses. Furthermore, the analgesic effect of the compound pertaining to the present invention is not suppressed even by concomitant use with a morphine antagonist, and said compound is believed to have a mechanism of effect differing from that of morphine. Thus, the compound pertaining to the present invention is advantageous in that its concomitant use with morphine secures a reliable relief from pain, and a gradual reduction in morphine dosage alleviates the side effects caused by a continued use of morphine. The present invention was achieved on the basis of such knowledge.

Thus, the present invention provides a novel compound possessing an aconitine chemical structure illustrated by the general formula (I) above and further provides an antipyretic/analgesic/anti-inflammatory agent containing as an active ingredient a compound possessing an aconitine chemical structure illustrated by the general formula (I) above, or a salt thereof.

The present invention is described in detail in the following.

The novel compound pertaining to the present invention, illustrated by the general formula (I) above, can be manufactured by substituting various substituents for a substituent bound to the 3 position, the 15 position, the 14 position, or a nitrogen atom in a starting material of: aconitine, mesaconitine, jesaconitine, hypaconitine, 14-O-benzoylaconine, 14-O-benzoylmesaconine, 14-O-anisoylaconine, or 14-O-benzoylhypaconine, illustrated by formula (II) below; pyroaconitine, pyromesaconitine, pyrojesaconitine, pyrohypaconitine, 16-epipyroaconitine, 16-epipyromesaconitine, 16-epipyrojesaconitine, 16-epipyrohypaconitine, or other known compounds having an aconitine chemical structure, illustrated by formula (III) below; or compounds with a carbonyl group at the 15 position reduced to form a hydroxyl group, illustrated by formula (III) below.

| Compound | $R_1$ | $R_2$ | $R_3$ | $R_4$ |
|---|---|---|---|---|
| Aconitine | OH | OAc | H | Et |
| Mesaconitine | OH | OAc | H | Me |
| Jesaconitine | OH | OAc | OMe | Et |
| Hypaconitine | H | OAc | H | Me |
| 14-O-benzoylaconine | OH | OH | H | Et |
| 14-O-benzoylmesaconine | OH | OH | H | Me |
| 14-O-anisoylaconine | OH | OH | OMe | Et |
| 14-O-benzoylhypaconine | H | OH | H | Me |

Ac: $CH_3CO$, Me: $CH_3$, Et: $CH_3CH_2$

| Compound | $R_1$ | $R_2$ | $R_3$ | * |
|---|---|---|---|---|
| Pyroaconitine | OH | H | Et | β |
| Pyromesaconitine | OH | H | Me | β |
| Pyrojesaconitine | OH | OMe | Et | β |
| Pyrohypaconitine | H | H | Me | β |
| 16-epipyroaconitine | OH | H | Et | α |
| 16-epipyromesaconitine | OH | H | Me | α |
| 16-epipyrojesaconitine | OH | OMe | Et | α |
| 16-epipyrohypaconitine | H | H | Me | α |

Me: $CH_3$, Et: $CH_3CH_2$,
*Indicates position 16 $OCH_3$ placement

Acylation of a hydroxyl group can be carried out by bringing about a reaction in an appropriate solvent such as pyridine between the relevant compound and, ordinarily, an acid anhydride or acid chloride used when esterifying a hydroxyl group. When acetic anhydride is used as an acetylating agent and, among the above-mentioned starting materials, the starting material used is a compound with a hydroxyl group present at the 3 position and the 15 position and no acetyl group present at the 8 position, the acetylation reaction prefers the 15 position, and a 15-acetyl compound can be obtained as a primary product.

An alkyl substituent bonded to a nitrogen atom can be replaced with another substituent by first reacting the corresponding compound and an appropriate oxidizing agent such as potassium permanganate in an appropriate solvent such as acetone to afford an N-dealkylated product. The N-dealkylated product obtained is then reacted with an alkylating agent such as an alkyl halide in order to introduce the desired alkyl group.

A carbonyl reduction reaction can be carried out by dissolving the corresponding compound in an appropriate solvent such as ethanol or acetic acid, then performing catalytic hydrogenation at room temperature or under heating, with a catalyst of platinum oxide, palladium carbon, or Raney nickel or the like. A carbonyl reduction reaction can also be accomplished by dissolving the corresponding compound in an appropriate solvent such as ether, adding a metal hydride complex such as lithium aluminum hydride, sodium boron hydride, lithium t-butoxyaluminum hydride, or lithium trimethoxyaluminum hydride, and agitating under appropriate temperature conditions.

Various combinations of each of the above-noted reactions may be carried out to afford a compound illustrated by the foregoing general formula (I).

The compound pertaining to the present invention may also form salts with inorganic acids such as hydrochloric aid, sulfuric acid, and hydrobromic acid, or organic acids such as oxalic acid, succinic acid, tartaric acid, citric acid, and ascorbic acid.

Next are given manufacturing examples of compounds pertaining to the present invention, illustrated by general formula (I). Analytical data for compounds obtained in each example appears after the description of the example. The pharmacologic effect, toxicity, and other information concerning each compound is also given in Tables 7 through 13 appearing below. Table 1 provides a cross reference of compound numbers and the name thereof for the following tables.

EXAMPLE 1

Aconitine 500 mg was dissolved in 5 ml of 5% potassium hydroxide/methanol and this solution was stirred at room temperature for 10 hours. After methanol in the reaction mixture was distilled off, the residue was dissolved in 5 ml of ice water. This solution was subjected to column chromatography on 100 ml of Amberlite XAD-2 (Nippon Organo), which had been washed with methanol and water in that order. After the column was washed by water until the washings were free from alkalinity, it was eluted with 1000 ml of methanol. The elute was concentrated to dryness under reduced pressure to afford 480 mg of residue containing aconine. This residue was dissolved in 10 ml of distilled pyridine. To this solution, 0.3 ml of p-chlorobenzoyl chloride was added and the mixture was stirred at −18° C. for 10 minutes. After reaction, the reaction mixture was chromatographed on a silica gel column (50 g), eluting with chloroform (150 ml), 5% methanol/chloroform (150 ml), 10% methanol/chloroform (150 ml), 15% methanol/chloroform (150 ml) and 20% methanol/chloroform in that order. The elutes with 10% methanol/chloroform and 15% methanol/chloroform were mixed and concentrated to dryness under reduced pressure. The residue was subjected to column chromatography on 150 g of silica gel, and eluted with ammonia-saturated chloroform for separation and purification. The so purified residue was recrystallized from acetone-hexane to afford 400 mg of 14-O-p-chlorobenzoylaconine.

EXAMPLE 2

To 14-O-p-chlorobenzoylaconine 300 mg obtained in the same manner as in Example 1, 10 ml of acetic anhydride and 5 ml of pyridine were added and the mixture was stirred at room temperature for 1 hour. After the reaction mixture was poured into ice water and made alkaline with 10% ammonia water, it was extracted three times with 100 ml of ether. The ether extract was washed with water, dried over anhydrous sodium sulfate and concentrated to dryness under reduced pressure. The residue was subjected to preparative thin-layer chromatography for separation and purification with ammonia-saturated chloroform/ether (1:1) to afford 145 mg of 15-O-acetyl-14-O-p-chlorobenzoylaconine.

EXAMPLE 3

15-O-Acetyl-14-O-p-chlorobenzoylaconine 208 mg was dissolved in 25 ml of acetone. To this solution, 25 ml of aqueous potassium permanganate solution (127 mg in 25 ml of acetone/water (1:1)) was added and the mixture was stirred at room temperature for 1.5 hours. After reaction, the reaction mixture was acidified with 2N sulfuric acid under ice cooled temperature and , to this solution, sodium sulfite was added until this mixture solution became clear. Next, the reaction mixture was concentrated under reduced pressure. After this concentrated solution was made alkaline with 10% ammonia water, it was extracted three times with 100 ml of chloroform. The chloroform layer was washed with water, dried over anhydrous sodium sulfate and concentrated to dryness under reduced pressure. The residue was subjected to column chromatography on 10 g of silica gel with 5% methanol/ammonia-saturated chloroform-for separation and purification to afford 93.4 mg of de-N-ethyl-15-O-acetyl-14-O-p-chiorobenzoylaconine.

EXAMPLE 4

14-O-p-chlorobenzoylmesaconine 398 mg was obtained in the same manner as in Example 1, except for the use of 500 mg of mesaconitine as a substitute for aconitine in Example 1.

EXAMPLE 5

To 100 mg of 14-O-p-chlorobenzoylmesaconine, 3.5 ml of acetyl anhydride and 2 ml of pyridine were added and the mixture was stirred at room temperature for 1 hour. After reaction, the reaction mixture was poured into ice water, made alkaline with 10% ammonia water and extracted three times with 50 ml of ether. The ether extract was washed with water, dried over anhydrous sodium sulfate and concentrated to dryness under reduced pressure. The residue was subjected to preparative thin-layer chromatography for separation and purification with ammonia-saturated chloroform/ether (1:1) to afford 50.3 mg of 15-O-acetyl-14-O-p-chlorobenzoylmesaconine.

EXAMPLE 6

De-N-ethyl-15-O-acetyl-14-O-p-chlorobenzoylaconine 50 mg obtained in the same manner as in Example 3 was dissolved in 2 ml of the mixture of methanol/ether (1:1). To this solution, 65 mg of calcium carbonate and 0.2 ml of propyl iodide were added and the mixture was heated under reflux for 2 hours. After cooling, the reaction mixture was filtrated off to remove insolubles and concentrated to dryness under reduced pressure. The residue was subjected to column chromatography on 5 g of silica gel for separation and purification with 5% methanol/ammonia-saturated chloroform to afford 28 mg of de-N-ethyl-N-propyl-15-O-acetyl-14-O-p-chlorobenzoylaconine.

EXAMPLE 7

(1) Under reduced pressure (1.5–2 mmHg), mesaconitine 100 mg was fused at 200° C. for 30 minutes. After cooling, the reaction mixture was subjected to column chromatography on 10 g of silica gel for separation and purification with 5% methanol/chloroform to afford 56 mg of pyromesaconitine.

(2) Pyromesaconitine 50 mg was dissolved in 5 ml of dehydrated tetrahydrofuran. To this solution, 5 ml of tetrahydrofuran solution of litium alminium trimethoxy hydride which had been produced by stirring of tetrahydrofuran suspention (5 ml) of litium alminum hydride (144 mg) with 0.46 ml of methanol at room temperature was dropped slowly under the condition of −70° C. After the solution was stirred at −70° C. for 1 hour, followed by further stirring at room temperature for additional 1 hour. Next, to the reaction mixture, tetrahydrofuran containing a little water was added slowly under cooling with ice and the solution was filtrated off to remove the insolubles. The obtained filtrate was concentrated to dryness under reduced pressure. The residue was subjected to column chromatography on 15 g of silica gel for separation and purification with 5% methanol/ammonia-saturated chloroform to afford 46 mg of 8-deoxymesaconine.

(3) 8-Deoxymesaconine 45 mg was dissolved in 0.5 ml of pyridine. To this solution, 0.5 ml of the solution of p-chlorobenzoyl chloride/pyridine (0.05 ml/0.5 ml) was dropped and the mixture was stirred at room temperature for 2.5 hours. After reaction, the reaction mixture was poured into ice water, acidified with 10% hydrochloric acid and washed two times with 50 ml of ether. After the hydrochloric acid layer was made alkaline with 10% ammonia water, it was extracted three times with 50 ml of ether. The ether layer was washed with water, dried over anhydrous sodium sulfate and concentrated to dryness under reduced pressure. The residue was subjected to column chromatography on 5 g of alumina for separation and purification with chloroform to afford 32 mg of 8-deoxy-14-O-p-chlorobenzoylmesaconine.

EXAMPLE 8

(1) Under reduced pressure(1.5–2 mmHg), aconitine 100 mg was fused at 200° C. for 30 minutes. After cooling, the reaction mixture was subjected to column chromatography on 10 g of silica gel for separation and purification with 5% methanol/chloroform to afford 60 mg of pyroaconitine.

(2) 8-Deoxyaconine 47 mg was obtained in the same manner as in Example 7(2), except for the use of 50 mg of pyroaconitine as a substitute for pyromesaconitine in Example 7 (2).

(3) 8-Deoxy-14-O-p-chlorobenzoylaconine 36 mg was obtained in the same manner as in Example 7 (3), except for the use of 45 mg of 8-deoxyaconine as a substitute for 8-deoxymesaconine in Example 7(3)

EXAMPLE 9

Pyroaconitine 50 mg was dissolved in 5 ml of 5% potassium hydroxide/methanol and this solution was stirred at room temperature for 3 hours. After reaction, the reaction mixture was concentrated to dryness under reduced pressure and the residue was dissolved in 10 ml of water. This aqueous solution was subjected to column chromatography on 100 ml of Amberlite XAD-2 (Nippon Organo). This column was washed by water until the washings were free from alkalinity and then eluted with methanol. The residue was subjected to column chromatography on 10 g of silica gel for separation and purification with 10% methanol/ammonia-saturated chloroform to afford 43 mg of 16-epi-pyroaconine.

EXAMPLE 10

(1) 16-Epi-pyroaconine 45 mg was obtained in the same manner as in Example 9.

(2) 8-Deoxy-16-epi-aconine 36 mg was obtained in the same manner as in Example 7(2), except for the use of 40 mg of 16-epi-pyroaconine as a substitute for pyromesaconitine in Example 7 (2).

(3) 8-Deoxy-16-epi-14-O-p-chlorobenzoylaconine 28.6 mg was obtained in the same manner as in Example 7(3), except for the use of 36 mg of 8-deoxy-16-epi-aconine as a substitute for 8-deoxymesaconine in Example 7 (3).

EXAMPLE 11

(1) 16-Epi-pyromesaconine 42 mg was obtained in the same manner as in Example 9, except for the use of 50 mg of pyromesaconitine as a substitute for pyroaconitine in Example 9.

(2) 8-Deoxy-16-epi-mesaconine 37.6 mg was obtained in the same manner as in Example 7(2), except for the use of 42 mg of 16-epi-pyromesaconine as a substitute for pyromesaconitine in Example 7(2).

(3) 8-Deoxy-16-epi-14-O-p-chlorobenzoylmesaconine 33 mg was obtained in the same manner as in Example 7(3), except for the use of 37 mg of 8-deoxy-16-epi-mesaconine as a substitute for 8-deoxymesaconine in Example 7(3).

EXAMPLE 12

To 100 mg of 14-O-p-chlorobenzoylaconine, 0.5 ml of acetic anhydride and 1 ml of pyridine were added. The mixture was stirred at room temperature for 12 hours. After reaction, the reaction mixture was poured into ice water. This solution was made alkaline with 10% ammonia water and then extracted three times with 50 ml of ether. The ether layer was washed with water, dried over anhydrous sodium sulfate and concentrated to dryness under reduced pressure. The residue was subjected to preparative thin-layer chromatography on silica gel for separation and purification with chloroform/methanol (50:1, at ammonia-saturated condition) to afford 74 mg of 3,15-di-O-acetyl-14-O-p-chlorobenzoylaconine.

EXAMPLE 13

3,15-Di-O-acetyl-14-O-p-chlorobenzoylmesaconine 32 mg was obtained in the same manner as in Example 12, except for the use of 65 mg of 14-O-p-chlorobenzoylmesaconine as a substitute for 14-O-p-chlorobenzoylaconine in Example 12.

EXAMPLE 14

(1) 14-O-p-chlorobenzoylhypaconine 380 mg was obtained in the same manner as in Example 1, except for the use of 500 mg of hypaconitine as a substitute for aconitine in Example 1.

(2) 15-O- Acetyl-14-O-p-chlorobenzoylhypaconine 53 mg was obtained in the same manner as in Example 12, except for the use of 100 mg of 14-0-p-chlorobenzoylhypaconine as a substitute for 14-O-p-chlorobenzoylaconine in Example 12.

EXAMPLE 15

15-O-Acetyl-8-deoxy-14-O-p-chlorobenzoylmesaconine 21 mg was obtained in the same manner as in Example 5, except for the use of 30 mg of 8-deoxy-14-O-p-chlorobenzoylmesaconine as a substitute for 14-0-p-chlorobenzoylmesaconine in Example 5.

EXAMPLE 16

15-O-Acetyl-8-deoxy-14-O-p-chlorobenzoylaconine 22 mg was obtained in the same manner as in Example 5, except for the use of 30 mg of 8-deoxy-14-O-p-chlorobenzoylaconine as a substitute for 14-O-p-chlorobenzoylmesaconine in Example 5.

EXAMPLE 17

(1) 8-Deoxy-16-epi-14-O-p-chlorobenzoylaconine 30 mg was obtained in the same manner as in (1), (2) and (3) of Example 10.

(2) 15-O-Acetyl-8-deoxy-16-epi-14-O-p-chlorobenzoylaconine 24 mg was obtained in the same manner as in Example 5, except for the use of 30 mg of 8-deoxy-16-epi-14-O-p-chlorobenzoylaconine as a substitute for 14-O-p-chlorobenzoylmesaconine in Example 5.

EXAMPLE 18

De-N-ethyl-15-O-acetyl-8-deoxy-16-epi-14-O-p-chlorobenzoylaconine 12 mg was obtained in the same manner as in Example 3, except for the use of 24 mg of 15-O-acetyl-8-deoxy-16-epi-14-O-p-chlorobenzoylaconine as a substitute for 15-O-acetyl-14-O-p-chlorobenzoylaconine in Example 3.

EXAMPLE 19

(1) 8-Deoxy-16-epi-14-O-p-chlorobenzoylmesaconine 35 mg was obtained in the same manner as in (1), (2) and (3) of Example 11.

(2) 15-O-Acetyl-8-deoxy-16-epi-14-O-p-chlorobenzoylmesaconine 27 mg was obtained in the same manner as in Example 5, except for the use of 35 mg of 8-deoxy-16-epi-14-O-p-chlorobenzoylmesaconine as a substitute for 14-O-p-chlorobenzoylmesaconine in Example 5.

EXAMPLE 20

De-N-ethyl-N-propyl-15-O-acetyl-8-deoxy-16-epi-14-O-p-chlorobenzoylaconine 25 mg was obtained in the same manner as in Example 6, except for the use of 50 mg of de-N-ethyl-15-O-acetyl-8-deoxy-16-epi-14-O-p-chlorobenzoylaconine as a substitute for de-N-ethyl-15-O-acetyl-14-O-p-chlorobenzoylaconine in Example 6.

TABLE 1

Substance name and number

| No. of substance | Substance name |
|---|---|
| (1) | 15-O-acetyl-14-O-p-chlorobenzoylmesaconine |
| (2) | 15-O-acetyl-14-O-p-chlorobenzoylaconine |
| (3) | de-N-ethyl-N-propyl-15-O-acetyl-14-O-p-chlorobenzoylaconine |
| (4) | 3,15-di-O-acetyl-14-O-p-chlorobenzoylaconine |
| (5) | 3,15-di-O-acetyl-14-O-p-chlorobenzoylmesaconine |
| (6) | 15-O-acetyl-14-O-p-chlorobenzoylhypaconine |
| (7) | 15-O-acetyl-8-deoxy-14-O-p-chlorobenzoylmesaconine |
| (8) | 15-O-acetyl-8-deoxy-14-O-p-chlorobenzoylaconine |
| (9) | 15-O-acetyl-8-deoxy-16-epi-14-O-p-chlorobenzoylmesaconine |
| (10) | 15-O-acetyl-8-deoxy-16-epi-14-O-p-chlorobenzoylaconine |
| (11) | de-N-ethyl-N-propyl-15-O-acetyl-8-deoxy-16-epi-14-O-p-chlorobenzoylaconine |

TABLE 2

1) Analysis of Infrared (IR) spectra

| No. of substance | IR (KBr, cm$^{-1}$) |
|---|---|
| (1) | 1715 |
| (2) | 1710 |
| (3) | 1715 |
| (4) | 1715 |
| (5) | 1715 |
| (6) | 1720 |
| (7) | 1710 |
| (8) | 1717 |
| (9) | 1717 |
| (10) | 1710 |
| (11) | 1715 |

TABLE 3

2) Analysis of Ultraviolet (UV) spectra

| No. of substance | $\lambda EtOH_{nm(\log \epsilon)}^{max}$ |
|---|---|
| (1) | 246 (3.97) |
| (2) | 246 (3.98) |
| (3) | 246 (3.98) |
| (4) | 246 (4.03) |
| (5) | 246 (4.01) |
| (6) | 246 (3.97) |
| (7) | 246 (4.00) |
| (8) | 246 (4.01) |
| (9) | 246 (3.97) |
| (10) | 246 (4.01) |
| (11) | 246 (3.98) |

TABLE 4

3) Analysis of $^1$H-NMR spectra

| No. of substance | δ, ppm (CDCl$_3$) |
|---|---|
| (1) | 7.98 (2H, d, J=8.7Hz) and 7.43 (2H, d, J=8.7Hz) (p-chlorobenzoyl group), 5.34 (1H, d, J=6.0Hz) (C15-H), 4.92 (1H, d, J=5.1Hz) (C14-H), 3.72 (3H, s), 3.31 (3H, s), 3.29 (3H, s) and 3.26 (3H, s) (OCH3 at C1, C6, C16 and C18), 2.35 (3H, s) (CH3 at the nitrogen atom), 2.23 (3H, s) (CH3 of acetyl group at C15) |
| (2) | 7.98 (2H, d, J=8.7Hz) and 7.42 (2H, d, J=8.7Hz) (p-chlorobenzoyl group), 5.33 (1H, d, J=6.0Hz) (C15-H), 4.92 (1H, d, J=5.1Hz) (C14-H), 3.72 (3H, s), 3.31 (3H, s), 3.30 (3H, s) and 3.25 (3H, s) (OCH3 at C1, C6, C16 and C18), 2.22 (3H, s) (CH3 of acetyl group at C15), 1.14 (3H, t, J=7.2Hz) (CH3 of ethyl group at the nitrogen atom) |
| (3) | 7.99 (2H, d, J=8.7Hz) and 7.42 (2H, d, J=8.7Hz) (p-chlorobenzoyl group), 5.32 (1H, d, J=6.3Hz) (C15-H), 4.93 (1H, d, J=5.1Hz) (C14-H), 3.71 (3H, s), 3.30 (3H, s), 3.29 (3H, s) and 3.26 (3H, s) (OCH3 at C1, C6, C16 and C18), 2.24 (3H, s) (CH3 of acetyl group at C15), 0.93 (3H, t, J=7.0Hz) (CH3 of propyl group at the nitrogen atom) |
| (4) | 7.99 (2H, d, J=8.7Hz) and 7.41 (2H, d, J=8.7Hz) (p-chlorobenzoyl group), 5.36 (1H, d, J=6.0Hz) (C15-H), 4.92 (1H, d, J=5.1Hz) (C14-H), 4.90 (1H, dd, J=10.4, 5.3Hz) (C3-H), 3.60 (3H, s), 3.26 (3H, s), 3.24 (3H, s) and 3.21 (3H, s) (OCH3 at C1, C6, C16 and C18), 2.21 (3H, s) and 2.06 (3H, s) (CH3 of acetyl group), 1.14 (3H, t, J=7.2Hz) (CH3 of ethyl group at the nitrogen atom) |
| (5) | 7.99 (2H, d, J=8.7Hz) and 7.42 (2H, d, J=8.7Hz) (p-chlorobenzoyl group), 5.35 (1H, d, J=6.0Hz) (C15-H), 4.91 (1H, d, J=5.1Hz) (C14-H), 4.90 (1H, dd, J=10.5, 5.2Hz) (C3-H), 3.60 (3H, s), 3.28 (3H, s), 3.25 (3H, s) and 3.21 (3H, s) (OCH3 at C1, C6, C16 and C18), 2.33 (3H, s) (CH3 at the nitrogen atom), 2.22 (3H, s) and 2.06 (3H, s) (CH3 of acetyl group) |
| (6) | 7.99 (2H, d, J=8.7Hz) and 7.42 (2H, d, J=8.7Hz) (p-chlorobenzoyl group), 5.35 (1H, d, J=6.0Hz) (C15-H), 4.93 (1H, d, J=5.4Hz) (C14-H), 3.60 (3H, s), 3.30 (3H, s), 3.29 (3H, s) and 3.22 (3H, s) (OCH3 at C1, C6, C16 and C18), 2.31 (3H, s) (CH3 at the nitrogen atom), 2.22 (3H, s) (CH3 of acetyl group) |
| (7) | 7.97 (2H, d, J=8.8Hz) and 7.43 (2H, d, J=8.8Hz) (p-chlorobenzoyl group), 4.85 (1H, d, J=5.0Hz) (C14-H), 4.65 (1H, dd, J=12.0, 6.0Hz) (C15-H), 3.69 (3H, s), 3.30 (3H, s), 3.28 (3H, s) and 3.25 (3H, s) (OCH3 at C1, C6, C16 and C18), 2.35 (3H, s) (CH3 at the nitrogen atom), 2.22 (3H, s) (CH3 of acetyl group) |
| (8) | 7.97 (2H, d, J=8.8Hz) and 7.43 (2H, d, J=8.8Hz) (p-chlorobenzoyl group), 4.86 (1H, d, J=5.0Hz) (C14-H), 4.64 (1H, dd, J=12.0, 6.0Hz) (C15-H), 3.70 (3H, s), 3.31 (3H, s), 3.28 (3H, s) and 3.25 (3H, s) (OCH3 at C1, C6, C16 and C18), 2.23 (3H, s) (CH3 of acetyl group), 1.11 (3H, t, J=7.0Hz) (CH3 of ethyl group at the nitrogen atom) |
| (9) | 7.98 (2H, d, J=8.9Hz) and 7.42 (2H, d, J=8.9Hz) (p-chlorobenzoyl group), 5.00 (1H, d, J=4.0Hz) (C14-H), 4.73 (1H, t, J=12.0Hz) (C15-H), 3.67 (3H, s), 3.30 (3H, s), 3.29 (3H, s) and 3.25 (3H, s) (OCH3 at C1, C6, C16 and C18), 2.35 (3H, s) (CH3 at the nitrogen atom), 2.24 (3H, s) (CH3 of acetyl group) |
| (10) | 7.98 (2H, d, J=8.9Hz) and 7.42 (2H, d, J=8.9Hz) (p-chlorobenzoyl group), 4.98 (1H, d, J=4.0Hz) (C14-H), 4.74 (1H, t, J=12.0Hz) (C15-H), 3.66 (3H, s), 3.31 (3H, s), 3.30 (3H, s) and 3.26 (3H, s) (OCH3 at C1, C6, C16 and C18), 2.25 (3H, s) (CH3 of acetyl group), 1.12 (3H, t, J=7.0Hz) (CH3 of ethyl group at the nitrogen atom) |
| (11) | 7.98 (2H, d, J=8.9Hz) and 7.42 (2H, d, J=8.9Hz) (p-chlorobenzoyl group), 4.98 (1H, d, J=4.1Hz) (C14-H), 4.75 (1H, t, J=11.8Hz) (C15-H), 3.67 (3H, s), 3.31 (3H, s), 3.30 (3H, s) and 3.26 (3H, s) (OCH3 at C1, C6, C16 and C18), 2.25 (3H, s) (CH3 of acetyl group), 0.98 (3H, t, J=7.0Hz) (CH3 of propyl group at the nitrogen atom) |

TABLE 5

4) Analysis of ¹³C-NMR spectra

| No. of substance | δ, ppm (CDCl₃) |
|---|---|
| (1) | 173.4 (carbonyl of acetyl group at C15), 165.4 (carbonyl of p-chlorobenzoyl group), 139.5, 131.1, 128.8 and 128.4 (p-chlorobenzoyl group), 88.5, 87.7, 82.3, 81.9, 79.3, 76.5, 76.0, 74.5 and 72.2 (C16, C15, C6, C1, C14, C18, C8, C13 and C3), 60.9, 59.1, 57.6 and 56.0 (C16', C18', C6' and C1'), 42.3 (CH3 at the nitrogen atom), 21.0 (CH3 of acetyl group) |
| (2) | 173.4 (carbonyl of acetyl group at C15), 165.4 (carbonyl of p-chlorobenzoyl group), 139.5, 131.1, 128.7 and 128.4 (p-chlorobenzoyl group), 88.6, 87.6, 82.3, 82.0, 79.3, 76.5, 76.1, 74.6 and 72.3 (C16, C15, C6, C1, C14, C18, C8, C13 and C3), 60.9, 59.1, 57.6 and 56.0 (C16', C18', C6' and C1'), 47.1 (CH2 of ethyl group at the nitrogen atom), 20.9 (CH3 of acetyl group), 13.4 (CH3 of ethyl group at the nitrogen atom) |
| (3) | 173.3 (carbonyl of acetyl group at C15), 165.4 (carbonyl of p-chlorobenzoyl group), 139.4, 131.1, 128.7 and 128.4 (p-chlorobenzoyl group), 88.5, 87.6, 82.4, 82.0, 79.3, 76.5, 76.1, 74.5 and 72.3 (C16, C15, C6, C1, C14, C18, C8, C13 and C3), 60.9, 59.1, 57.6 and 56.0 (C16', C18', C6' and C1'), 21.0 (CH3 of acetyl group), 10.3 (CH3 of propyl group at the nitrogen atom) |
| (4) | 173.3 and 170.1 (carbonyl of acetyl group), 165.3 (carbonyl of p-chlorobenzoyl group), 139.3, 131.1, 128.7 and 128.4 (p-chlorobenzoyl group), 88.7, 87.5, 82.8, 81.9, 79.3, 76.5, 74.7, 71.7 and 71.5 (C16, C15, C6, C1, C14, C8, C13, C18 and C3), 61.4, 58.7, 57.8 and 56.2 (C16', C18', C6' and C1'), 47.4 (CH2 of ethyl group at the nitrogen atom), 21.1 and 20.9 (CH3 of acetyl group), 13.5 (CH3 of ethyl group at the nitrogen atom) |
| (5) | 173.3 and 170.1 (carbonyl of acetyl group), 165.3 (carbonyl of p-chlorobenzoyl group), 139.3, 131.1, 128.7 and 128.4 (p-chlorobenzoyl group), 88.6, 87.6, 82.6, 81.9, 79.2, 76.4, 74.7, 71.7 and 71.3 (C16, C15, C6, C1, C14, C8, C13, C18 and C3), 61.3, 58.7, 57.8 and 56.5 (C16', C18', C6' and C1'), 42.5 (CH3 at the nitrogen atom), 21.1 and 21.0 (CH3 of acetyl group) |
| (6) | 173.4 (carbonyl of acetyl group), 165.3 (carbonyl of p-chlorobenzoyl group), 139.3, 131.1, 128.7 and 128.5 (p-chlorobenzoyl group), 88.6, 87.6, 85.0, 82.3, 80.3, 79.3, 76.4 and 74.7 (C16, C15, C6, C1, C18, C14, C8 and C13), 61.3, 59.0, 57.6 and 56.4 (C16', C18', C6' and C1'), 42.7 (CH3 at the nitrogen atom), 21.0 (CH3 of acetyl group) |
| (7) | 173.3 (carbonyl of acetyl group), 165.2 (carbonyl of p-chlorobenzoyl group), 139.6, 131.1, 128.8 and 128.1 (p-chlorobenzoyl group), 92.0, 85.0, 83.6, 80.9, 80.7, 77.3, 75.0 and 71.6 (C16, C6, C1, C15, C14, C18, C13 and C3), 61.7, 59.1, 57.8 and 56.0 (C16', C18', C6' and C1'), 42.3 (CH3 at the nitrogen atom), 20.8 (CH3 of acetyl group) |
| (8) | 173.2 (carbonyl of acetyl group), 165.0 (carbonyl of p-chlorobenzoyl group), 139.7, 131.1, 128.9 and 128.1 (p-chlorobenzoyl group), 92.1, 85.0, 83.6, 80.8, 80.7, 77.3, 75.0 and 71.5 (C16, C6, C1, C15, C14, C18, C13 and C3), 61.7, 59.0, 57.8 and 56.0 (C16', C18', C6' and C1'), 47.1 (CH2 of ethyl group at the nitrogen atom), 20.8 (CH3 of acetyl group), 13.4 (CH3 of ethyl group at the nitrogen atom) |
| (9) | 173.3 (carbonyl of acetyl group), 165.1 (carbonyl of p-chlorobenzoyl group), 139.4, 131.1, 128.7 and 128.4 (p-chlorobenzoyl group), 88.9, 85.0, 82.4, 80.8, 79.9, 77.5, 75.9 and 71.8 (C16, C6, C1, C15, C14, C18, C13 and C3), 62.2, 59.1, 58.0 and 56.2 (C16', C18', C6' and C1'), 42.3 (CH3 at the nitrogen atom), 21.0 (CH3 of acetyl group) |
| (10) | 173.3 (carbonyl of acetyl group), 165.1 (carbonyl of p-chlorobenzoyl group), 139.4, 131.1, 128.7 and 128.4 (p-chlorobenzoyl group), 88.9, 85.1, 82.6, 80.7, 79.8, 77.4, 76.0 and 71.8 (C16, C6, C1, C15, C14, C18, C13 and C3), 62.2, 59.1, 58.0 and 55.8 (C16', C18', C6' and C1'), 47.4 (CH2 of ethyl group at the nitrogen atom), 21.0 (CH3 of acetyl group), 13.4 (CH3 of ethyl group at the nitrogen atom) |
| (11) | 173.2 (carbonyl of acetyl group), 165.0 (carbonyl of p-chlorobenzoyl group), 139.4, 131.1, 128.7 and 128.4 (p-chlorobenzoyl group), 89.0, 85.1, 82.6, 80.7, 79.9, 77.4, 75.9 and 71.8 (C16, C6, C1, C15, C14, C18, C13 and C3), 62.1, 59.1, 58.0 and 55.9 (C16', C18', C6' and C1'), 21.0 (CH3 of acetyl group), 10.3 (CH3 of propyl group at the nitrogen atom) |

TABLE 6

5) Analysis of Mass spectra

| No. of substance | M⁺ (m/z) |
|---|---|
| (1) | 665, 667 |
| (2) | 679, 681 |
| (3) | 693, 695 |
| (4) | 721, 723 |
| (5) | 707, 709 |
| (6) | 649, 651 |
| (7) | 649, 651 |
| (8) | 663, 665 |
| (9) | 649, 651 |
| (10) | 663, 665 |
| (11) | 677, 679 |

Next, example of experiment with respect to the pharmacological property and acute toxicity of the compound shown in formula (I) mentioned above are described below.

Experiment Example 1

(1) Measurement of Analgesic Activity by the Tail-Pressure Method

Std:ddY Strain male mice (20–25 g) were fasted for one day before the experiment, and were used. After test compounds shown in Table 1 was formed to a salt with tartaric acid, this salt was dissolved in 0.9% physiological saline solutions at the rate of 10 mg/10 ml to give the test compound solution. As a control, 0.9% physiological saline solution was used. A tail-pressure apparatus was used in this experiments. Before the administration of test compounds, the pain threshold was measured twice at intervals of 30 minutes and those mice indicating a pain threshold of 50 to 100 mmHg were selected and used. The pain threshold of each mouse was measured at 1 hour after test compound solution mentioned above was administered at 10 ml/kg, s.c. 0.9% Physiological saline solution as a control was administered at 10 ml/kg, s.c . The results were described as an inhibition rate (%) obtained from the following equation. Cutoff level of pressure was defined to be 230 mmHg for the prevention of the damage of mouse tail. The results are shown in Table 7 described later. It was demonstrated in Table 7 that the compounds of this invention had a potent analgesic activity and its strength was higher than that of 14-O-p-chlorobenzoylaconine.

Inhibition rate $(\%) = (A-B) \times 100 / (C-B)$

A: Pain threshold (mmHg) after the administration of test compound solution

B: Pain threshold (mmHg) before the administration of test compound solution

C: Cutoff pressure (230 mmHg)

(2) Comparison with Morphine

Std:ddY Strain male mice (20–25 g) were fasted for one day before the experiment, and were used. In this experiment, the tartaric acid salt of a compound of number (2) in Table 1 and morphine hydrochloride as a possitive control were used. This tartaric acid salt was dissolved in 0.9% physiological saline solution at the rates of 5 mg/2 ml, 3 mg/2 ml and 1 mg/2 ml. Morphine hydrochloride was dissolved in 0.9% physiological saline solution at the rates of 5 mg/2 ml, 3 mg/2 ml and 1 mg/2 ml. As a negative control, 0.9% phisiological saline solution was used. A tail-pressure apparatus was used in this experiments. Before the administration of test compounds, the pain threshold was measured twice at intervals of 30 minutes and those mice indicating a pain threshold of 50 to 100 mmHg were selected and used. The pain threshold of each mouse was measured at 10, 20 and 30 minutes after test compound solution mentioned above was administered at 2 ml/kg, i.v. 0.9% Physiological saline solution as a control was administered i.v. The results were described as an inhibition rate (%) indicating in the preceding paragraph (1). The results are shown in Table 8 described later. It was demonstrated in Table 8 that the compound of this invention had an equal analgesic activity in its strength to morphine.

(3) Experiment Combined with Morphine Administration

Std:ddY Strain male mice (20–25 g) were fasted for one day before the experiment, and were used. In this experiment, the tartaric acid salt of a compound of number (2) in Table 1 and morphine hydrochloride were used. The tartaric acid salt of a compound of number (2) was dissolved in 0.9% physiological saline solution at the rate of 7 mg/10 ml. Morphine hydrochloride was dissolved in 0.9% physiological saline solution at the rates of 5 mg/2 ml, 3 mg/2 ml and 1 mg/2 ml. As a control, 0.9% phisiological saline solution was used. A tail-pressure apparatus was used in this experiments. Before the administration of test compounds, the pain threshold was measured twice at intervals of 30 minutes and those mice indicating a pain threshold of 50 to 100 mmHg were selected and used. Mice was divided in the following four groups, (i) control group, (ii) the administration group of the tartaric acid salt of a compound of number (2), (iii) the administration group of morphine hydrochloride and (iv) the combined administration group with the tartaric acid salt of a compound of number (2) and morphine hydrochloride. In the administration group of the tartaric acid salt of a compound of number (2), 0.9% physiological saline solution of this tartaric acid salt mentioned above was injected s.c. at the rate of 10 ml/kg and, 30 minutes later, 0.9% physiological saline solution was injected i.v. at the rate of 2 ml/kg. In the administration group of morphine hydrochloride, 0.9% physiological saline solution was injected s.c. at the rate of 10 ml/kg and, 30 minutes later, the above physiological saline solution of morphine hydrochloride was injected i.v. at the rate of 2 ml/kg. In the combined administration group with the tartaric acid salt of a compound of number (2) and morphine hydrochloride, the above physiological saline solution of the tartaric acid salt of a compound of number (2) was injected s.c. at the rate of 10 ml/kg and, 30 minutes later, the above physiological saline solution of morphine hydrochloride was injected i.v. at the rate of 2 ml/kg. In control group, 0.9% physiological saline solution was injected s.c. at the rate of 10 ml/kg and, 30 minutes later, 0.9% physiological saline solution was injected i.v. at the rate of 2 ml/kg. Each pain threshold was measured 10, 20 and 30 minutes after an intravenous injection. The results were described in Table 9 as an inhibition rate (%) indicating in the preceding paragraph (1). It was demonstrated in Table 9 that the compound of this invention greatly potentiated the analgesic effect of morphine.

(4) Experiment Combined with Morphine Antagonist

Std:ddY Strain male mice (20–25 g) were fasted for one day before the experiment, and were used. In this experiment, the tartaric acid salt of a compound of number (2) in Table 1, morphine hydrochloride and levallorphan hydrochloride of an opioid antagonist were used. The tartaric acid salt of a compound of number (2) was dissolved in 0.9% physiological saline solution at the rate of 10 mg/2 ml. Morphine hydrochloride was dissolved in 0.9% physiological saline solution at the rate of 10 mg/2 ml. Levallorphan hydrochloride was dissolved in 0.9% physiological saline solution at the rate of 1 mg/10 ml. As a control, 0.9% physiological saline solution was used. A tail-pressure apparatus was used in this experiments. Before the administration of levallorphan hydrochloride, the pain threshold was measured twice at intervals of 30 minutes and those mice indicating a pain threshold of 50 to 100 mmHg were selected and used. Levallorphan hydrochloride solution mentioned above was administered s.c. at the rate of 10 ml/kg and, 30 minutes later, the above tartaric acid salt solution compound of number (2) or morphine hydrochloride solution was injected i.v. at the rate of 2 ml/kg, respectively. Each pain threshold was measured 10, 20 and 30 minutes after an intravenous injection. In control group, 0.9% physiological saline solution was injected i.v. at the rate of 2 ml/kg at 30 minutes after s.c. administration at 10 ml/kg of 0.9% physiological saline solution. In the single administration group of levallorphan hydrochloride, levallorphan hydrochloride solution mentioned above was administered s.c. at the rate of 10 ml/kg and, 30 minutes later, 0.9% physiological saline solution was injected i.v. at the rate of 2 ml/kg. The results were described in Table 10 as an inhibition rate (%) indicating in the preceding paragraph (1). It was demonstrated in Table 10 that the analgesic action of a compound of this invention was not affected by the combination use with levallorphan, whereas that of morphine was inhibited by the combination use with levallorphan.

Experiment Example 2

Measurement of Analgesic Activity by the Hot-Plate Method

Std:ddY Strain male mice (20–25 g) were fasted for one day before the experiment, and were used. After compounds shown in Table 1 were formed to the tartaric acid salts, these compounds were dissolved in 0.9% physiologocal saline solution at the rate of 10 mg/10 ml, respectively and these solution were used as test compound solution. In a control, 0.9% physiological saline solution was used. Mice were placed on a cyrindric hot plate (diameter: 22 cm, height: 11 cm) made of copper which was fixed in a water bath adjusted to 52° C. so that each animal's four paws came into contact with the plate and the time taken to show the nociceptive response (licking) as an index of pain was measured. Mice showing response latency above 25 seconds were excluded from the experiment. To prevent a burn damage of mouse tissue by heating, cutoff time of 50 seconds was defined. The results were described as an inhibition rate (%) obtained from the following equation.

Inhibition rate $(\%)=(A-B)\times 100/(50-B)$

A: Response latency (seconds) after the administration of test compound solution B: Response latency (seconds) before the administration of test compound solution 50: Cutoff time The results are shown in Table 11 described later. It was demonstrated in Table 11 that the compounds of this invention had a potent analgesic activity and its strength was higher than that of 14-O-p-chlorobenzoylaconine.

Experiment Example 3

Measurement of Antipyretic Activity on Yeast-Induced Fever in Rats

Wistar Strain male rats (150–190 g) were fasted for one day before the experiment, and were used. Compounds of number (1) and (2) in Table 1 were formed to the tartaric acid salt and these salts were dissolved in 0.9% physiological saline solution at the rate of 10 mg/10 ml and these solution were used as test compound solution. In a control, 0.9% physiological saline solution was used. After rat rectal temperature was measured, 1 ml/100 g of body weight of 7.5% yeast/0.9% physiological saline solution was injected s.c. at dorsal position. Then, rat rectal temperature was measured at 4 hour after the injection of yeast and rats showing the increase rectal temperature by 1 degree or more were selected and used. Test compound solution was administered s.c. at 5 hours after the injection of yeast. The rectal temperature was measured 2 hours after the administration of test compound solution. The results were described with the difference between the rectal temperature before and after the administration of test compound solution. The results are shown in Table 12. It was demonstrated in Table 12 that the compounds of this invention had an antipyretic action.

Experiment Example 4

Measurement of Antiinflammatory Activity by the Carrageenin-Induced Hind Paw Edema Std:ddY Strain male mice (20–25 g) were fasted for one day before the experiment, and were used. After test compounds shown in Table 1 was formed to a salt with tartaric acid, this salt was dissolved in sterilized and distilled water at the rate of 30 mg/10 ml to give the test compound solution. As a control, sterilized and distilled water was used. One hour after the oral administration of test compound solutions, 25 µl of λ-carrageenin suspended in 0.9% physiological saline solution (0.5 mg/25 µl) was injected s.c. under the plantar surface of the right hind paw of a mouse and 25 µl of 0.9% physiological saline solution was injected s.c. under the plantar surface of the left hind paw of the same mouse. Three hours and five hours after carrageenin injection, the volume of the paw was measured with a dial gauge calliper. To the control group, One hour after the oral administration of sterilized and distilled water at the rate of 10 ml/kg, 25 µl of λ-carrageenin (0.5 mg/25 µl) suspended in 0.9% physiological saline solution was injected s.c. under the plantar surface of the right hind paw of a mouse and 25 µl of 0.9% physiological saline solution was injected s.c. under the plantar surface of the left hind paw of the same mouse and the later operation was done in the same manner as in the test compound dosing group mentioned above. The results were described as a swelling rate (%) obtained from the following equation.

Swelling rate (%)=(R–L)×100/L

R: the thickness of the right hind paw
L: the thickness of the left hind paw

The results are shown in Table 13 described later. It was demonstrated in Table 13 that the compounds of this invention had an inhibitory action against the carrageenin-induced paw edema.

Experiment Example 5

Acute Toxicity

Std:ddY Strain male mice (20–25 g) were fasted for one day before the experiment, and were used. The solutions of test compounds were prepared in the same manner as in Experiment example 4 (30 mg/10 ml). The lethal number of mice was counted during 72 hours after test compound solution was administered p.o. Consequently, no death of mice was seen at p.o. administration of 30 mg/kg and the compounds of this invention were thus found to be low in toxicity.

TABLE 7

Analgesic activity (tail-pressure method)

| Compound | inhibition rate (%) (*) |
|---|---|
| control | 1 ± 3 |
| 14-O-p-chlorobenzoylaconine | 10 ± 4 |
| (1) | 48 ± 12 |
| (2) | 43 ± 10 |
| (3) | 36 ± 10 |
| (4) | 29 ± 8 |
| (5) | 40 ± 10 |
| (6) | 27 ± 11 |
| (7) | 35 ± 10 |
| (8) | 26 ± 7 |
| (9) | 31 ± 12 |
| (10) | 23 ± 7 |
| (11) | 25 ± 8 |

*mean ± standard error.

TABLE 8

Comparison with morphine

| Compound | Dose (i.v., mg/kg) | Inhibition rate (%) (mean ± standard error) Time after administration (minutes) | | |
|---|---|---|---|---|
| | | 10 | 20 | 30 |
| control | — | –2 ± 3 | 2 ± 5 | 0 ± 5 |
| morphine | 1 | 1 ± 2 | 2 ± 2 | 2 ± 1 |
| | 3 | 13 ± 7 | 18 ± 10 | 12 ± 8 |
| | 5 | 38 ± 12 | 30 ± 10 | 29 ± 12 |
| (2) | 1 | 5 ± 4 | 4 ± 4 | 2 ± 3 |
| | 3 | 14 ± 15 | 16 ± 10 | 12 ± 12 |
| | 5 | 38 ± 13 | 27 ± 6 | 22 ± 7 |

TABLE 9

Experiment combined with morphine administration

| Dose of morphine (i.v., mg/kg) | Dose of compound* combined with morphine administration (s.c., mg/kg) | Inhibition rate (%, mean ± standard error) Time after morphine administration (min) | | |
|---|---|---|---|---|
| | | 10 | 20 | 30 |
| control | 0 | –4 ± 4 | 3 ± 4 | 2 ± 3 |
| 0 | 7 | 30 ± 11 | 35 ± 12 | 37 ± 11 |
| 1 | 0 | 2 ± 2 | 3 ± 4 | 1 ± 2 |
| 3 | 0 | 11 ± 8 | 15 ± 9 | 10 ± 6 |
| 5 | 0 | 36 ± 10 | 32 ± 11 | 26 ± 8 |
| 1 | 7 | 31 ± 12 | 36 ± 10 | 32 ± 7 |
| 3 | 7 | 47 ± 8 | 50 ± 9 | 38 ± 12 |
| 5 | 7 | 73 ± 13 | 77 ± 9 | 78 ± 9 | n = 7.
*: Compound of substance number (2) described in Table 1.

TABLE 10

Experiment combined with morphine antagonist

| Dose of levallorphan (mg/kg) | Dose of compound combined with levallorphan (mg/kg, i.v.) | | Inhibition rate (%, mean ± standard error) Time after morphine administration (min) | | |
|---|---|---|---|---|---|
| | (a) | (b) | 10 | 20 | 30 |
| 0 | 0 | 0 | −2 ± 3 | 1 ± 2 | −3 ± 3 |
| 1 | 0 | 0 | 3 ± 4 | −3 ± 4 | 1 ± 3 |
| 0 | 10 | 0 | 70 ± 13 | 73 ± 9 | 65 ± 12 |
| 1 | 10 | 0 | 10 ± 1* | 10 ± 7* | 20 ± 6* |
| 0 | 0 | 10 | 85 ± 15 | 80 ± 20 | 65 ± 21 |
| 1 | 0 | 10 | 86 ± 25 | 77 ± 14 | 67 ± 22 |

(a): morphine,
(b): Compound of substance number (2) described in Table 1.
*: Significantly different from the administration group of morphine alone, P < 0.01.

TABLE 11

Analgesic activity (hot-plate method)

| Compound | Inhibition rate (%, mean ± standard error) |
|---|---|
| control | 3 ± 5 |
| 14-O-p-chlorobenzoylaconine | 17 ± 7 |
| (1) | 52 ± 12 |
| (2) | 76 ± 11 |
| (3) | 39 ± 11 |
| (4) | 35 ± 9 |
| (5) | 37 ± 10 |
| (6) | 46 ± 8 |
| (7) | 49 ± 11 |
| (8) | 48 ± 8 |
| (9) | 46 ± 7 |
| (10) | 40 ± 10 |
| (11) | 34 ± 9 |

TABLE 12

Antipyretic Action

| Compound | Dose (mg/kg, s.c.) | Change of rectal temperature (°C.) |
|---|---|---|
| control | 0 | 1.9 ± 0.2 |
| (1) | 1 | 1.3 ± 0.1 |
| | 3 | 0.2 ± 0.1 |
| | 10 | 0.2 ± 0.2 |
| (2) | 1 | 1.5 ± 0.2 |
| | 3 | 0.5 ± 0.2 |
| | 10 | 0.3 ± 0.1 |

TABLE 13

Antiinflammatory activity

| | Swelling rate (%, mean ± standard error) | |
|---|---|---|
| Compound | 3 hour | 5 hour |
| control | 80 ± 10 | 92 ± 11 |
| (d) | 57 ± 8 | 63 ± 9 |
| (1) | 49 ± 2 | 52 ± 6 |
| (2) | 40 ± 9 | 46 ± 9 |
| (3) | 42 ± 10 | 54 ± 8 |
| (4) | 50 ± 7 | 55 ± 9 |
| (5) | 43 ± 10 | 58 ± 10 |
| (6) | 46 ± 5 | 60 ± 5 |
| (7) | 43 ± 8 | 48 ± 8 |
| (8) | 41 ± 5 | 55 ± 8 |
| (9) | 44 ± 7 | 56 ± 7 |

TABLE 13-continued

Antiinflammatory activity

| | Swelling rate (%, mean ± standard error) | |
|---|---|---|
| Compound | 3 hour | 5 hour |
| (10) | 49 ± 6 | 49 ± 11 |
| (11) | 50 ± 5 | 52 ± 9 |

(d): 14-O-p-chlorobenzoylaconine   n = 6.
All compounds in the above Table were dosed p.o. at 30 mg/kg.

The dose of the compound of the formula (I) for clinical use as analgesic/anti-inflammatory agent according to the invention is preferably 1–800 mg/day for adults. The agent according to the present invention is presented for actual application after formed into desired dosage forms by conventional methods using customarily used carriers or excipients. Wherever appropriate or necessary, the compound of the present invention may be used in the form of a salt thereof for achieving its pharmaceutical effect or facilitating the preparation of dosage forms.

Oral preparations such as tablets, powders, granules and capsules may contain conventional excipients such as calcium carbonate, magnesium carbonate, calcium phosphate, corn starch, potato starch, sugar, lactose, talc, magnesium stearate and gum arabic. Tablets may be coated by conventional methods. Oral liquid preparations may be aqueous or oily suspensions, solutions, syrups, elixirs etc.

For injectable preparations, the compound of the formula (I) may be used in the form of a salt thereof, and preferably reconstituted upon use. Such preparations may contain different adjuvants such as suspending, stabilizing or dispersing agents. They may contain sterilized distilled water, refined oils such as peanut oil and corn oil, non-aqueous solvents, polyethylene glycol, polypropylene glycol, etc.

Preparations for rectal administration are presented in the form of compositions for suppository and may contain pharmaceutical carriers well known in the art such as polyethylene glycol, lanolin and coconut oil.

Preparations for topical application are presented in the form of compositions for ointment, plaster or poultice and may contain pharmaceutical carriers well known in the art such as vaseline, paraffin, hydrous lanolin, plastibase, kaolin, bentonite, talc, aluminum silicate, propylene glycol, sorbitol, hydrophilic petrolatum, macrogols, wax, resin, purified lanolin, gum, glycerin, gelatin, polyacrylic acid, polyacrylic acid salt, polyvinyl alcohol, polyvinyl pyrrolidone and polyethylene oxide.

I claim:

1. A compound of the general formula (I) possessing an aconitine structure, or a salt thereof

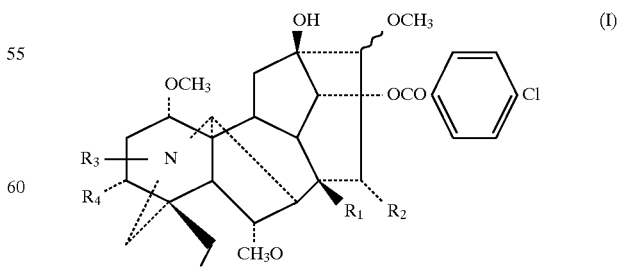

wherein,
$R_1$ is a hydrogen atom or hydroxyl group;
$R_2$ is an acetyloxy group;

$R_3$ is an alkyl having 1–4 carbon atoms; and $R_4$ is a hydrogen atom, a hydroxyl group, or an acetyloxy group.

2. An antipyretic or analgesic or anti-inflammatory composition comprising a compound of the general formula (I), or a salt thereof as claimed in claim 1 as an active ingredient and at least one excipient.

3. A compound according to claim 1, which is not in the form of a salt.

4. A compound according to claim 1, which is in the form of a salt.

5. A compound according to claim 4, wherein the salt is a salt of an inorganic acid or an organic acid.

6. A compound according to claim 4, wherein the salt is a salt of hydrochloric acid, sulfuric acid, hydrobromic acid, oxalic acid, succinic acid, tartaric acid, citric acid, or ascorbic acid.

7. A compound according to claim 1, which is 15-O-acetyl-14-O-p-chlorobenzoylmesaconine or a salt thereof.

8. A compound according to claim 1, which is 15-O-acetyl-14-O-p-chlorobenzoylaconine or a salt thereof.

9. A compound according to claim 1, which is de-N-ethyl-N-propyl-15-O-acetyl-14-O-p-chlorobenzoylaconine or a salt thereof.

10. A compound according to claim 1, which is 3,15-di-O-acetyl-14-O-p-chlorobenzoylaconine or a salt thereof.

11. A compound according to claim 1, which is 3,15-di-O-acetyl-14-O-p-chlorobenzoylmesaconine or a salt thereof.

12. A compound according to claim 1, which is 15-O-acetyl-14-O-p-chlorobenzoylhypacoine or a salt thereof.

13. A compound according to claim 1, which is 15-O-acetyl-8-deoxy-14-O-p-chlorobenzoylmesaconine or a salt thereof.

14. A compound according to claim 1, which is 15-O-acetyl-8-deoxy-14-O-p-chlorobenzoylaconine or a salt thereof.

15. A compound according to claim 1, which is 15-O-acetyl-8-deoxy-16-epi-14-O-p-chlorobenzoylmesaconine or a salt thereof.

16. A compound according to claim 1, which is 15-O-acetyl-8-deoxy-16-epi-14-O-p-chlorobenzoylaconine or a salt thereof.

17. A compound according to claim 1, which is de-N-ethyl-N-propyl-15-O-acetyl-8-deoxy-16-epi-14-O-p-chlorobenzoylaconine or a salt thereof.

18. A method of treating inflammation, pain, or fever in a mammal, comprising administering to a mammal in need thereof a compound as claimed in claim 1.

19. A method of treating inflammation, pain, or fever in a mammal, comprising administering to a mammal an composition as claimed in claim 2.

20. A method of treating a mammal according to claim 18, further comprising administering morphine or a salt thereof to the mammal.

* * * * *